United States Patent [19]

Sato et al.

[11] 4,386,120
[45] May 31, 1983

[54] PROCESS FOR PRODUCING POLYACRYLIC ACID SALT GRANULES EASILY SOLUBLE IN WATER

[75] Inventors: Fumihiro Sato, Urayasu; Masayuki Iwasaki; Takashi Terada, both of Yono; Hiroshi Ninomiya, Sayama; Minoru Nakada, Tokyo, all of Japan

[73] Assignee: Nippon Kayaku Kabushiki Kaisha, Tokyo, Japan

[21] Appl. No.: 276,808

[22] Filed: Jun. 24, 1981

Related U.S. Application Data

[63] Continuation of Ser. No. 109,858, Jan. 7, 1980.

[51] Int. Cl.³ .................. A61K 9/30; C08F 120/04
[52] U.S. Cl. .................................. 427/213; 424/81; 427/3; 264/DIG. 51
[58] Field of Search .................. 264/DIG. 51, 117; 424/81; 427/213, 3

[56] References Cited

U.S. PATENT DOCUMENTS 3,856,441 12/1974 Suzukawa ........................... 264/117
3,880,968 3/1975 Kasper ................................ 264/317
4,150,110 4/1979 Yoshida .............................. 424/81

FOREIGN PATENT DOCUMENTS 55-49135 3/1980 Japan ................................ 264/117
968751 7/1964 United Kingdom .
1471123 7/1975 United Kingdom .

*Primary Examiner*—Sam Silverberg
*Attorney, Agent, or Firm*—Henry C. Nields

[57] ABSTRACT

The present invention relates to a process for producing polyacrylic acid salt granules easily soluble in water characterized in that a water-soluble powder of polyacrylic acid salt is granulated according to fluidized bed granulation method while an aqueous solution of the polyacrylic acid salt of a viscosity of 50–700 c.p.s. is sprayed thereon.

12 Claims, No Drawings

PROCESS FOR PRODUCING POLYACRYLIC ACID SALT GRANULES EASILY SOLUBLE IN WATER

This is a continuation of application Ser. No. 109,858, filed Jan. 7, 1980.

BACKGOUND OF THE INVENTION

Water-soluble polyacrylic acid salts are now used widely as, for example, food additives such as thickening agent and emulsion stabilizer, aggregation or precipitation accelerator for industrial waste water, soil conditioner and cement additive. Recently, the water-soluble polyacrylic acid salts are expected as medicine for peptic ulcers, particularly peptic esophagitis ulcer.

The water-soluble polyacrylic acid salts are obtained generally in the form of a gel polymer by the aqueous solution polymerization. Usually, the gel polymer is used in the form of powder obtained by drying the same and crushing it into particle size of about 100–200 mesh. In many cases, the powder is used practically in the form of an aqueous solution. However, in dissolving the powder in water to form the aqueous solution, undissolved lumps are formed frequently, which are hardly dissolved therein. Further, finely divided particles contained in the powder are apt to be scattered during the work at a working site and the particles thus scattered adhere to the surroundings in the workshop. The particles having an extremely high hygroscopicity thus form a sticky extraneous matter to cause environmental pollution in the workshop unfavorably.

For overcoming those defects, there has been proposed a process wherein the dried gel polymer is crushed into particles of 20–65 mesh (Tyler) for convenience in the use. However, according to this process, undissolved lumps are formed due to the large particle size and a considerably long period of time is required for the complete dissolution of the particles to form a homogeneous solution, since the particles are hard, though the dissolution time is still shorter than that required in case of using powder. As processes for overcoming said defect, there have been known processes wherein sodium polyacrylate powder is kneaded with water or a hydrous, hydrophilic organic solvent and the mixture is then dried and then crushed or, alternatively, the mixture is granulated and then dried (Japanese Patent Laid-Open No. 83681/1974) and wherein a powder of alkali metal salt of polyacrylic acid is contacted with water in a hydrophilic organic solvent and the resulting mass is dried and then crushed into aggregated granules (Japanese Patent Laid-Open No. 133, 251/1975). However, according to those processes, particle size distribution of the product extends over a wide range from powder to granules and yield of particles of a high solubility (16–80 mesh) (Tyler) is as low as about 65%, since the mass once produced is crushed. Another defect of those processes is that the production operations are complicated. Said process disclosed in the specification of Japanese Patent Laid-Open No. 83681/1974 wherein the granules are obtained by granulating the kneaded mixture and then drying the same is not suitable for an industrial scale, since the granulation of the mixture is difficult.

After intensive investigations on the production of granules of a polyacrylic acid salt of a highly soluble size (16–80 mesh) in a high yield in an easy manner, the inventors have found that if a water-soluble powder of polyacrylic acid salt is granulated by the fluidized bed granulation method in the presence of an aqueous solution of polyacrylic acid salt as binder, granules of a highly soluble size of 16–80 mesh can be obtained in a yield as high as about 95% and, particularly, granules of an extremely highly soluble size of 16–48 mesh can be obtained in a yield of about 80%.

DETAILED DESCRIPTION OF THE INVENTION

The present invention has been completed on the basis of said finding.

The water-soluble powder of polyacrylic acid salts are not particularly limited. They include, for example, alkali metal salts such as sodium and potassium salts and salts with bases such as ammonium compounds of an average molecular weight of 500,000–10,000,000, preferably 2,000,000–10,000,000. Those salts may be partially replaced with other alkali metal salts or ammonium compounds or with alkaline earth metal salts such as calcium, magnesium and barium or trivalent metals such as aluminum and iron.

As for particle size distribution, the salts have a particle size of 20–325 mesh (Tyler), preferably 48–200 mesh and an average particle diameter of 100–200 μm, preferably 140–170 μm.

The polyacrylic acid salt to be sprayed is preferably the same compound as the polyacrylic acid salt to be granulated, the former being used in an amount of 0.3–1 g, preferably 0.35–0.8 g per kilogram of the latter. In case sodium polyacrylate is used, the amount thereof is preferably 0.35–0.5 g per kilogram of the latter. Viscosity of the aqueous solution of polyacrylic acid salt is 50–700 c.p.s., preferably 150–350 c.p.s.

The fluidized bed granulation device is not particularly limited and the device of any type such as fluidized bed type, modified fluidized bed type or jet bed type can be used.

In carrying out the granulation process according to the present invention, a powder of polyacrylic acid salt is fluidized in the fluidized bed granulating device, an aqueous solution of polyacrylic acid salt is sprayed thereon to form granules and then the granules are dried.

Granulation temperature is 40°–80° C., preferably 45°–70° C.

The aqueous polyacrylic acid salt solution is sprayed for 5–90 seconds, preferably 10–80 seconds at intervals of longer than 3 seconds, preferably longer than 5 seconds.

Thus obtained granules are sieved to obtain the product of 16–80 mesh in a yield of about 95% or the product of 16–48 mesh in a yield of about 80%.

When a binder other than the polyacrylic acid salt was used, yield of the product of 16–80 mesh did not reach 95% even though the granulation conditions were varied.

The following experiments prove that easily soluble granules of 16–80 mesh can be obtained in a high yield by the granulation process of the present invention.

EXPERIMENTS

Determination of particle size distribution (yield) of the granules (1) Preparation of samples 15.5 kilograms of sodium polyacrylate (hereinafter referred to as PANA) having an average molecular weight of 8,000,000, a particle size distribution of 48–150 mesh and an average particle diameter of 158 μm were granulated using 7.5 liters of an aqueous binder solution shown in Table 1 in the same manner as in Example 1 given below to obtain a sample.

TABLE 1

| Sample | Binder | Conc. (W/V %) | Viscosity (c.p.s.) | Remarks |
| --- | --- | --- | --- | --- |
| A | PANA of average molecular weight of 8,000,000 | 0.075 | 298 | Sample of the present invention |
| B | Polyvinyl pyrrolidone | 20.0 | 215 | Control |
| C | Methylcellulose | 6.0 | 304 | Control |
| D | None (only water) | — | — | Control |

Aggregated granules prepared by the process described in Example 4 of Japanese Patent Laid-Open No. 133,251 were used as control sample E. Concrete method of the preparation was as follows: 1 Kilogram of PANA was added gradually to 11 liters of 30% aqueous ethanol under stirring. After stirring for about one hour, the mixture was filtered, dried and ground to obtain sample E.

(2) Method of experiment

Each sample was sieved through sieves of 16, 48 and 80 mesh (Tyler). The sample remaining on the sieve after the sieving was weighed and yield of the product was calculated according to the following formula:

$$\text{Yield} = \frac{\text{(Amount of granules remaining on the sieve)}}{\text{(Amount of PANA charged)} + \text{(Amount of binder used)}}$$

(3) Results of experiment

The results are shown in Table 2.

TABLE 2

| Sample | Particle size distribution | | | |
| --- | --- | --- | --- | --- |
|  | >16 mesh | 16–48 mesh | 48–80 mesh | <80 mesh |
| A | 1.7% | 80.1% | 14.6% | 3.6% |
| B | 7.6 | 63.2 | 9.0 | 20.2 |
| C | 3.2 | 60.5 | 8.3 | 28.0 |
| D | 4.7 | 59.1 | 7.9 | 28.3 |
| E | 6.3 | 54.7 | 10.2 | 28.8 |

It is apparent from the results that yield of sample A of the present invention having a highly soluble particle size of 16–80 mesh is 94.7% and that of particularly highly soluble particle size of 16–48 mesh of 80.1%, while yields of control sample E prepared according to the method of Japanese Patent Laid-Open No. 133,251/1975 were only 64.9% and 54.7%, respectively. Thus, yield of the product of particularly highly soluble particle size of 16–48 mesh was higher in the present invention by more than 40%.

Yields of control samples B and C prepared by using polyvinyl pyrrolidone and methylcellulose, respectively, as binder were only 63.2% and 60.5%, respectively for 16–48 mesh size, which yields were little different from yield of control sample D prepared by spraying only water (59.1%). On the other hand, yield of sample A prepared by using PANA as binder according to the present invention was as high as 80.1% which was higher than said yields of the control samples by more than 30%. This fact indicates superiority of PANA as binder.

Further, the sample of the present invention contains a fraction of a particle size of smaller than 80 mesh having a poor solubility in an amount of only 3.6%, while control samples B-E contains said fraction in an amount of 20.2-28.8%. Thus, it is understood that the process of the present invention is more excellent for the granulation of easily water-soluble polyacrylic acid salts.

The following examples further illustrate the granulation process of the present invention.

EXAMPLE 1

15.5 Kilograms of PANA having a particle size distribution of 48–150 mesh, an average particle diameter of 158 μm and an average molecular weight of 8,000,000 were charged in a fluidized bed granulation-drying device ®WSG-15R (a product of Ôkawara Seisakusho). 7.5 Liters of 0.075 W/V% aqueous solution (298 c.p.s.) of PANA of the same molecular weight as above were sprayed on PANA fluidized at 50° C. at a feed rate of 120 ml./min. under a spray pressure of 5 Kg/cm$^2$ to form granules. In the granulation, the spraying was effected for 20 seconds and then the whole was shaken for 5 seconds. These procedures were repeated in the initial stage (5 minutes). Thereafter, one minute spraying followed by 5 second shaking was repeated. After completion of the granulation, the granules were dried at 140° C. for 6 hours and then classified by sieving with a gyrosifter to collect granules of 16–48 mesh. Yield was 80.1% Dissolution time was 75 minutes which was equal to the solution time of aggregated granules produced by the process of Japanese Patent Laid-Open No. 133,251/1975.

Solution time of the starting powder of the granules was 320 minutes.

EXAMPLE 2

16.3 Kilograms of PANA powder having a particle size distribution of 48–200 mesh, an average particle diameter of 146 μm and an average molecular weight of 5,900,000 were charged in the same device as in Example 1. 8.1 Liters of 0.11 W/V % aqueous solution (311 c.p.s.) of PANA of the same molecular weight as above were sprayed on PANA fluidized at 55° C. at a feed rate of 100 ml./min. under a spray pressure of 4.5 Kg/cm$^2$ to form granules. Methods of spraying, drying and sieving were the same as in Example 1. Thus, granules of 16–48 mesh were obtained. Yield was 82.7%. Dissolution time was 70 minutes.

EXAMPLE 3

15.1 Kilograms of a water-soluble powder of polyacrylic acid salts (in which 50% of the carboxyl groups is sodium salt and 50% thereof is aluminum salt) having a particle size distribution of 48–200 mesh, an average particle diameter of 145 μm and an average molecular weight of 7,800,000 were granulated by spraying 7.7 liters of 0.15 W/V % aqueous solution of the same polyacrylic acid salts (267 c.p.s.) thereon at a feed rate of 90 ml./min. in the same manner as in Example 1 to obtain granules of 16–48 mesh. Yield was 80.9%. Dissolution time was 65 minutes.

Granules of a higher solubility could be obtained by subjecting the easily water-soluble polyacrylic acid salt granules produced by the process of the present invention to the treatment with a water-insoluble, water-permeable coating agent, i.e. semi-permeable coating agent, according to a coating method disclosed in the specification of U.S. Pat. No. 4,150,110.

EXAMPLE 4

15 Kilograms of the granules produced in Example 1 were subjected to spray coating treatment with a coating solution comprising 5 parts of ethylcellulose, 1 part of glycerol/fatty acid esters (O.D.O. ®, a product of Nisshin Seiyu Kabushiki Kaisha), 47 parts of methanol and 47 parts of methylene chloride till weight of the solid matter increased by 900 g. Thus, granules of a higher solubility were obtained. Dissolution time was 1 minute and 20 seconds.

What is claimed is:

1. A process for producing easily water-soluble sodium polyacrylate granules characterized in that sodium polyacrylate powder is granulated according to fluidized bed granulation method while an aqueous solution of the same compound as the said powder, is sprayed thereon and an amount of the compound sprayed is 0.3-0.8 g per kilogram of the said powder, and then the granules are dried and sieved to collect a fraction of 16-48 mesh.

2. A process for producing easily water-soluble sodium polyacrylate granules according to claim 1 wherein viscosity of the solution is 50-700 c.p.s.

3. A process for producing easily water-soluble sodium polyacrylate granules according to claim 1 wherein viscosity of the solution is 150-350 c.p.s.

4. A process for producing easily water-soluble polyacrylic acid salt granules according to claim 1 wherein the aqueous solution of polyacrylic acid salt is sprayed for 10-80 seconds at intervals of longer than 5 seconds.

5. A process for producing easily water-soluble sodium polyacrylate granules according to claim 1 wherein the sodium polyacrylate is sprayed for 5-90 seconds at intervals of longer than 3 seconds.

6. A process for producing easily water-soluble sodium polyacrylate according to claim 1 wherein granulation temperature is 40°-80° C.

7. A process for producing easily water-soluble polyacrylic acid salt granules according to claim 1 wherein the powder of polyacrylic acid salt has a particle size distribution of 20-325 mesh.

8. A process for producing easily water-soluble polyacrylic acid salt granules according to claim 1 wherein the powder of polyacrylic acid salt has a particle size distribution of 48-200 mesh.

9. A process for producing easily water-soluble polyacrylic acid salt granules according to claim 1 wherein the powder of polyacrylic acid salt has an average particle diameter of 100-200 $\mu$m.

10. A process for producing easily water-soluble polyacrylic acid salt granules according to claim 1 wherein the powder of polyacrylic acid salt has an average particle diameter of 140-170 $\mu$m.

11. A process for producing easily water-soluble polyacrylic acid salt granules according to claim 1 wherein granulation temperature is 45°-70° C.

12. A process for producing easily water-soluble sodium polyacrylate granules characterized in that sodium polyacrylate powder of an average molecular weight of 2,000,000-10,000,000 is granulated according to fluidized bed granulation method at 40°-80° C. while an aqueous solution of the same compound as the said powder, having a viscosity of 150-350 c.p.s., is sprayed thereon for 5-90 seconds at intervals of longer than 3 seconds and amount of the compound sprayed is 0.3-0.8 g per kilogram of the said powder, and then the granules are dried and sieved to collect a fraction of 16-48 mesh and the granules are coated with a water insoluble but a water-permeable coating agent.

* * * * *